(12) United States Patent
De Chazal et al.

(10) Patent No.: US 10,893,811 B2
(45) Date of Patent: Jan. 19, 2021

(54) SYSTEM AND METHOD FOR MONITORING CARDIORESPIRATORY PARAMETERS

(71) Applicant: ResMed Sensor Technologies Limited, Dublin (IE)

(72) Inventors: Philip De Chazal, Dublin (IE); Conor Hanley, Dun Laoghaire (IE); Conor Heneghan, San Jose, CA (US)

(73) Assignee: ResMed Sensor Technologies Limited

( * ) Notice: Subject to any disclaimer, the term of this patent is extended or adjusted under 35 U.S.C. 154(b) by 0 days.

(21) Appl. No.: 14/455,522

(22) Filed: Aug. 8, 2014

(65) Prior Publication Data

US 2014/0350361 A1 Nov. 27, 2014

Related U.S. Application Data

(63) Continuation of application No. 12/376,771, filed as application No. PCT/US2007/083155 on Oct. 31, 2007, now Pat. No. 8,834,364.

(Continued)

(51) Int. Cl.
*A61B 5/0205* (2006.01)
*A61B 5/05* (2006.01)
(Continued)

(52) U.S. Cl.
CPC .......... *A61B 5/0205* (2013.01); *A61B 5/0507* (2013.01); *A61B 5/1102* (2013.01);
(Continued)

(58) Field of Classification Search
CPC ... A61B 5/0205; A61B 5/0507; A61B 5/1102; A61B 5/113; A61B 5/6802; A61B 5/681; A61B 5/6895
See application file for complete search history.

(56) References Cited

U.S. PATENT DOCUMENTS 2,634,413 A * 4/1953 Potter ........................... 342/104
3,796,208 A   3/1974 Bloice
(Continued)

FOREIGN PATENT DOCUMENTS

| CN | 1155236 A | 7/1997 |
|---|---|---|
| JP | H01-115344 | 5/1989 |

(Continued)

OTHER PUBLICATIONS

European Examination Report for Application No. 07844765.3 dated Jul. 23, 2015.

(Continued)

*Primary Examiner* — Lynsey C Eiseman
*Assistant Examiner* — Jessandra F Hough
(74) *Attorney, Agent, or Firm* — Botos Churchill IP Law LLP

(57) ABSTRACT

An apparatus, system, and method is disclosed for monitoring the motion, breathing, heart rate of humans in a convenient and low-cost fashion, and for deriving and displaying useful measurements of cardiorespiratory performance from the measured signals. The motion, breathing, and heart rate signals are obtained through a processing applied to a raw signal obtained in a non-contact fashion, typically using a radio-frequency sensor. Processing into separate cardiac and respiratory components is described. The heart rate can be determined by using either spectral or time-domain processing. The respiratory rate can be calculated using spectral analysis. Processing to derive the heart rate, respiratory sinus arrhythmia, or a ventilatory threshold parameter using the system is described. The sensor, processing, and display can be incorporated in a single device which can be worn or held close to the body while exercising (e.g., in a wristwatch or mobile phone configuration), or alternately placed in a fixed piece of exercise equipment at some distance form the (Continued)

body (e.g., in a treadmill dash panel), and may also be integrated with other sensors, such as position locators.

47 Claims, 8 Drawing Sheets

Related U.S. Application Data

(60) Provisional application No. 60/863,862, filed on Nov. 1, 2006.

(51) Int. Cl.
  *A61B 5/113* (2006.01)
  *A61B 5/00* (2006.01)
  *A61B 5/11* (2006.01)

(52) U.S. Cl.
  CPC ............ *A61B 5/113* (2013.01); *A61B 5/681* (2013.01); *A61B 5/6802* (2013.01); *A61B 5/6895* (2013.01)

(56) References Cited

U.S. PATENT DOCUMENTS

| | | | |
|---|---|---|---|
| 3,911,899 A | 10/1975 | Hattes | |
| 3,993,995 A | 11/1976 | Kaplan et al. | |
| 4,085,740 A | 4/1978 | Allen, Jr. | |
| 4,513,748 A * | 4/1985 | Nowogrodzki | A61B 5/0507 600/430 |
| 4,926,868 A | 5/1990 | Larsen | |
| 4,958,638 A * | 9/1990 | Sharpe et al. | 600/407 |
| 5,361,070 A | 11/1994 | McEwan | |
| 5,519,400 A * | 5/1996 | McEwan | 342/28 |
| 5,521,600 A * | 5/1996 | McEwan | 342/27 |
| 5,549,113 A | 8/1996 | Halleck et al. | |
| 5,573,012 A * | 11/1996 | McEwan | 600/595 |
| 5,590,650 A | 1/1997 | Genova | |
| 5,682,164 A * | 10/1997 | McEwan | 342/27 |
| 5,766,208 A | 6/1998 | McEwan | |
| 5,828,333 A * | 10/1998 | Richardson et al. | 342/70 |
| 5,966,090 A * | 10/1999 | McEwan | 342/27 |
| 6,011,477 A | 1/2000 | Teodorescu et al. | |
| 6,062,216 A | 5/2000 | Corn | |
| 6,132,371 A | 10/2000 | Dempsey et al. | |
| 6,146,332 A | 11/2000 | Pinsonneault et al. | |
| 6,358,201 B1 * | 3/2002 | Childre et al. | 600/300 |
| 6,359,597 B2 | 3/2002 | Haj-Yousef | |
| 6,375,621 B1 * | 4/2002 | Sullivan | A61B 5/113 600/484 |
| 6,661,345 B1 * | 12/2003 | Bevan | G08B 21/06 340/575 |
| 6,834,251 B1 | 12/2004 | Fletcher | |
| 6,839,581 B1 | 1/2005 | El-Solh et al. | |
| 6,932,769 B2 | 8/2005 | Griffin et al. | |
| 7,196,629 B2 | 3/2007 | Ruoss et al. | |
| 7,199,749 B2 | 4/2007 | Greneker, III et al. | |
| 7,272,431 B2 | 9/2007 | McGrath | |
| 7,387,607 B2 | 6/2008 | Holt et al. | |
| 7,428,468 B2 | 9/2008 | Takemura et al. | |
| 7,473,228 B2 | 1/2009 | Griffin et al. | |
| 7,679,545 B2 | 3/2010 | Rausch et al. | |
| 7,898,455 B2 | 3/2011 | Rosenbury | |
| 7,956,755 B2 | 6/2011 | Lee et al. | |
| 8,026,840 B2 | 9/2011 | Dwelly et al. | |
| 8,398,538 B2 | 3/2013 | Dothie et al. | |
| 8,428,696 B2 | 4/2013 | Foo | |
| 8,454,528 B2 * | 6/2013 | Yuen | A61B 5/0205 600/534 |
| 2002/0082665 A1 * | 6/2002 | Haller | A61N 1/37264 607/60 |
| 2003/0009270 A1 * | 1/2003 | Breed | B60C 11/24 701/32.4 |
| 2003/0083559 A1 * | 5/2003 | Thompson | 600/372 |
| 2003/0092975 A1 | 5/2003 | Casscells et al. | |
| 2003/0201894 A1 * | 10/2003 | Li | B60N 2/002 340/573.1 |
| 2004/0012447 A1 * | 1/2004 | Nagaishi et al. | 331/2 |
| 2004/0073098 A1 * | 4/2004 | Geva et al. | 600/300 |
| 2004/0123667 A1 * | 7/2004 | McGrath | 73/704 |
| 2004/0127804 A1 | 7/2004 | Hatlesad et al. | |
| 2004/0147850 A1 * | 7/2004 | Amano | A61B 5/02028 600/513 |
| 2004/0249258 A1 * | 12/2004 | Tupin et al. | 600/407 |
| 2004/0249296 A1 | 12/2004 | Ellscheid et al. | |
| 2005/0073424 A1 * | 4/2005 | Ruoss | A61B 5/0507 340/686.6 |
| 2005/0113711 A1 | 5/2005 | Nakatani | |
| 2005/0119532 A1 | 6/2005 | Cloutier | |
| 2005/0128124 A1 | 6/2005 | Greneker et al. | |
| 2005/0143667 A1 | 6/2005 | Park et al. | |
| 2005/0240087 A1 * | 10/2005 | Keenan | A61B 5/0456 600/301 |
| 2005/0256415 A1 * | 11/2005 | Tan | A61B 5/0464 600/509 |
| 2006/0079164 A1 | 4/2006 | DeCastro et al. | |
| 2006/0111635 A1 | 5/2006 | Todros et al. | |
| 2006/0120586 A1 * | 6/2006 | Iatrou | A61B 6/032 382/131 |
| 2006/0136173 A1 * | 6/2006 | Case, Jr. | A63B 24/00 702/182 |
| 2006/0187111 A1 * | 8/2006 | Uchino | 342/70 |
| 2006/0189924 A1 * | 8/2006 | Blakley | A61B 5/00 604/66 |
| 2006/0217612 A1 * | 9/2006 | Ouchi | 600/407 |
| 2006/0241510 A1 | 10/2006 | Halperin et al. | |
| 2006/0270941 A1 * | 11/2006 | Xie | A61B 5/4818 600/529 |
| 2007/0027367 A1 | 2/2007 | Oliver et al. | |
| 2008/0074307 A1 * | 3/2008 | Boric-Lubecke | A61B 5/0205 342/28 |
| 2008/0157956 A1 | 7/2008 | Radivojevic et al. | |
| 2008/0234568 A1 | 9/2008 | Ouchi | |
| 2008/0269589 A1 | 10/2008 | Thijs et al. | |
| 2009/0203972 A1 * | 8/2009 | Heneghan | A61B 5/0507 600/301 |
| 2011/0015495 A1 | 1/2011 | Dothie et al. | |
| 2011/0112425 A1 | 5/2011 | Muhlsteff et al. | |
| 2012/0245479 A1 | 9/2012 | Ganesh et al. | |
| 2013/0006124 A1 | 1/2013 | Eyal et al. | |
| 2013/0053653 A1 | 2/2013 | Cuddihy et al. | |
| 2013/0135137 A1 | 5/2013 | Mulder et al. | |
| 2013/0172770 A1 | 7/2013 | Muehlsteff | |

FOREIGN PATENT DOCUMENTS

| | | |
|---|---|---|
| JP | H03-162636 | 7/1991 |
| JP | 5-47836 | 6/1993 |
| JP | 07017202 U | 3/1995 |
| JP | 2000083927 A | 3/2000 |
| JP | 2000102515 | 4/2000 |
| JP | 2002058659 A | 2/2002 |
| JP | 2002159453 A | 6/2002 |
| JP | 2003-135407 | 5/2003 |
| JP | 2003-290175 A | 10/2003 |
| JP | 2005270570 A | 10/2005 |
| JP | 2006068091 A | 3/2006 |
| JP | 2006081771 A | 3/2006 |
| JP | 2006149882 A | 6/2006 |
| JP | 2006255141 A | 9/2006 |
| JP | 2008503268 A | 2/2008 |
| WO | 9611630 A1 | 4/1996 |
| WO | 2004013611 A2 | 2/2004 |
| WO | 2004089208 A1 | 10/2004 |
| WO | 2004114193 A2 | 12/2004 |
| WO | 2005081011 | 9/2005 |
| WO | 2006003900 A1 | 1/2006 |
| WO | 2006113900 A2 | 10/2006 |
| WO | 2006115704 A1 | 11/2006 |
| WO | 2007143535 A3 | 12/2007 |
| WO | 2008096307 A1 | 8/2008 |
| WO | 2009124297 A1 | 10/2009 |
| WO | 2010048310 A1 | 4/2010 |

(56) References Cited

FOREIGN PATENT DOCUMENTS

| WO | 2010132850 A1 | 11/2010 |
|---|---|---|
| WO | 2012073183 A1 | 6/2012 |
| WO | 2013093712 A1 | 6/2013 |

OTHER PUBLICATIONS

European Office Action for Application No. 07844765.3 dated Mar. 7, 2016.
Australian Search Report for Australian Patent Application No. 2007317469, dated Jan. 6, 2010.
Barbon et al., "Maximal Exercise Testing for the Selection of Heart Transplantation Candidates—Limitation of Peak Oxygen Consumption," Chest, 1999;115:410-417.
Canadian Office Action for Canadian Patent Application No. 2,668,400, dated Jul. 21, 2010.
Chinese Office Action dated Jun. 21, 2011 of Chinese Appl. No. 200780046662.0 based on PCT/US2007/083155 (4 pages along with 5 page English Translation).
Chinese Office Action for Application No. 200780046662.0 dated Dec. 28, 2012.
Chinese Office Action for Application No. 200780046662.0 dated Feb. 8, 2014.
Chinese Office Action for Application No. 200780046662.0 dated Jul. 3, 2013.
Chinese Office Action for Application No. 200780046662.0 dated Jun. 6, 2014.
Chinese Office Action for Application No. 200780046662.0 dated Apr. 23, 2012 (8 pages long along with 6 page English translation).
De Meersman, Ronald E., "Respiratory sinus arrhythmia alteration following training in endurance athletes,", European Journal of Applied Physiology, vol. 64, No. 5, Sep. 1992, pp. 434-436.
European Extended Search Report for Application No. EP 11195916 dated Jun. 20, 2012.
European Office Action for Application No. 07844765.3 dated Feb. 11, 2014.
European Search report for European Patent Application No. 07844765.3, dated Nov. 2, 2009.
International Preliminary Report on Patentability for PCT International Application No. PCT/US2007/070196, dated Dec. 3, 2008.
International Search Report and Written Opinion of the International Searching Authority for PCT International Application No. PCT/US2007/070196, dated Feb. 22, 2008.
International Search Report, dated Mar. 20, 2008 regarding International Application No. PCT/US2007/083155, International Publication No. WO 2008/057883 A3, International Publication dated May 15, 2008.
James et al., "Independent component analysis for biomedical signals," Physiological Measurement vol. 26 (1), R15-R39, Feb 2005.
Japanese Office Action for Application No. 2009-535439 dated Apr. 2, 2013.
Japanese Office Action for Application No. 2009-535439 dated May 7, 2014.
Written Opinion of the International Searching Authority for PCT International Application No. PCT/US2007/083155, dated Mar. 20, 2008.
EP Communication for Application No. 07844765.3 dated Oct. 10, 2014.
Japanese Office Action for Application No. 2014-203540 dated Jun. 30, 2015.
"Estimation of sleep stages based on heart rate fluctuation and body movement", SICE 2004 Annual IEEE, Piscataway, NJ, USA, vol. 3, Aug. 4, 2004.
EP Communication dated Feb. 5, 2020 for EP Application No. 11195916.9.
EP Search Report dated Feb. 3, 2020 for EP Application No. 19188946.8.
Boric-Lubecke, O , et al., "Range Correlation and I/Q Performance Benefits in Single-Chip Silicon Doppler Radars for Noncontact Cardiopulmonary Monitoring", IEEE Transactions on Microwave Theory and Echniques, IEEE Service Center, vol. 52, No. 3, Mar. 1, 2004.
Yifan, Chen , et al., "Non-Invasive Respiration Rate Estimation Using Ultra-Wideband Distributed Cognitive Radar System", pp. 920-923, XP031389984, ISBN: 978-1-4244-0032-4.

* cited by examiner degree of RSA is associated with health, and will change in response to exercise and changes in diet (see for example, "Respiratory sinus arrhythmia alteration following training in endurance athletes," by Ronald E. De Meersman, published in *European Journal of Applied Physiology*, vol. 64, no. 5, September 1992, pages 434-436). However, in order to quantify RSA, simultaneous measurements of heart rate and respiration are desirable.

SYSTEM AND METHOD FOR MONITORING CARDIORESPIRATORY PARAMETERS

CROSS-REFERENCE TO RELATED APPLICATIONS

This continuation application claims the benefit of U.S. application Ser. No. 12/376,771, filed Feb. 6, 2009 which was a U.S. National Stage Application under 35 U.S.C. § 371 of International Application No. PCT/US07/083155, filed Oct. 31, 2007. PCT/US07/083155 claims benefit of U.S. Provisional Application No. 60/863,862, filed Nov. 1, 2006. The entire contents of both of these applications are incorporated herein by reference.

This disclosure relates to the monitoring of motion, breathing, and heart rate of living beings, e.g., humans, in a convenient and low-cost fashion that is useful, for example, in the assessment of cardiorespiratory markers of fitness and activity, and more particularly to an apparatus, system, and method for acquiring, processing and displaying the corresponding information in a easily understandable format. In this application, reference is made to a system which can measure motion, breathing and heart rate as a cardiorespiratory monitoring device or system.

BACKGROUND

Monitoring of heart rate and respiration is of interest in assessing the performance of cardiorespiratory systems. For example, measurements of heart rate are useful when assessing fitness levels of humans, as there are well-established guidelines for physiologically normal ranges of heart rate in response to differing levels of activity. Measurements of heart rate are widely used in fitness training schedules. For example, an exercise which maintains heart rate in a range between 100 and 120 beats per minute (bpm) may be useful for fat-burning and endurance building, whereas a competitive athlete may wish to undertake activity which raises the heart rate level to 160-180 bpm. Moreover, levels have been determined which reliably adjust for age and gender, so that individuals interested in a structured cardiovascular fitness program can monitor their progress quantitatively. Accordingly, it is desirable to be able to measure heart rate in a variety of settings. However, reliable measurement of heart rate in exercise conditions poses certain technical challenges. While running or cycling, motion artifact can corrupt heart rate measurements. While swimming, electrical measurement of heart rate can be difficult due to the conducting nature of water.

In addition to heart rate, breathing rate, depth and patterns are useful indicators of the overall status of the cardiorespiratory system. It is well observed that breathing rate increases in response to exercise, but the rate of increase (or decrease during an exercise recovery period) is a marker of overall cardiorespiratory health. For persons with compromised cardiorespiratory status, who might experience dyspnoea, for example, the elevated respiratory rate is a useful marker of status.

Individual measurements of heart rate and respiration are of value, but in addition useful measurements can be derived from combinations of these measurements which provide overall markers. For example, it is known that breathing directly modulates heart rate through a physiological mechanism called respiratory sinus arrhythmia (RSA), in which the heart speeds up during inspiration, and decreases during expiration. RSA is particularly pronounced in young people, and tends to decline with age. However, in general, a high Other useful parameters of cardiorespiratory fitness are the anaerobic threshold (AT) and ventilatory threshold (VT). The anaerobic threshold is the point at which the cardiorespiratory system is not providing sufficient oxygen to the muscles for the muscles' energy needs to be fully met by aerobic metabolic processes. Accordingly, the body uses its glycogen stores in an anaerobic metabolic process to maintain muscle output. At this point, the person has reached their maximum oxygen uptake, and will shortly become too fatigued to maintain their activity level (the maximum oxygen uptake is referred to as $VO_{2,max}$). To measure AT accurately requires specialized laboratory equipment and blood sampling, so while this is used as a "gold standard", it is not practical for widespread use by individuals interested in fitness. The ventilatory threshold is related physiologically to the anaerobic threshold. It is a point at which the response of minute ventilation (liters/min of air breathed) to exercise intensity becomes nonlinear, and is marked by a substantial increase in breathing rate. From an aerobic fitness point of view, it has been shown that the anaerobic threshold and the ventilatory threshold are strongly correlated. Since the goal of many fitness programs is to increase AT, it is useful to be able to use VT as a reliable surrogate marker. The cardiorespiratory monitor can be used to estimate VT by using combinations of respiration rate and heart rate. This will provide utility to the user of the monitor, as they can track the trends in their VT over long time periods (e.g., over the course of a fitness training program).

In the clinical setting, it is also useful to have reliable markers of cardiovascular fitness. For example, people suffering from heart failure have high exercise intolerance. Some subjects with heart failure are candidates for heart transplant, but given the scarcity of available hearts, doctors must prioritize patients in order of the severity of their disease. Again, for such cases, measurements of VT can be useful in assessing the overall health of the patient. A discussion of the challenges of assessing cardiorespiratory markers for assessing heart transplantation candidates is given in D. Ramos-Barbón, D. Fitchett, W. J. Gibbons, D. A. Latter, and R. D. Levy, "Maximal Exercise Testing for the Selection of Heart Transplantation Candidates—Limitation of Peak Oxygen Consumption," Chest. 1999; 115:410-417.

A large variety of techniques exist for measurement of heart rate for the purposes of assessing cardiorespiratory fitness. Surface lead electrocardiograms (ECGs) are a highly accurate way of capturing cardiac electrical activity, and hence heart rate. However, they require that the subject attach gelled electrodes to the chest region, and also carry or wear the associated electronic processing and/or recording device. So generally, full ECG measurement is restricted to clinical applications.

More convenient techniques for electrocardiogram measurement have been introduced which trade off signal quality for convenience, and are now widely used in commercially available heart rate fitness monitors. These techniques use electrodes which are embedded in conductive textiles which are placed in proximity to the skin. Typically, the textiles form part of a chest band worn around the thorax at the level of the chest. Since the conductivity of the textile material is dependent on moisture content, these sensors work best when the person is exercising vigorously and the skin is moistened with sweat (alternatively users can apply some conducting gel to ensure good electrical measurement). The disadvantage of this system is the requirement for the person to wear the chest band, and the reduced signal quality when the person's skin is not moist.

Another technique for assessing heart rate during exercise is to use pulse oximetry, which measures the changes in reflected/transmitted light through blood vessels. A characteristic photoplethysmogram can be generated in which each cardiac contraction is visible as a distinct pulse. However, pulse oximetry methods for measuring heart rate are limited by motion artifacts and poor perfusion characteristics. The power requirements of the light emitting diodes used in oximeters can also be a limiting factor in the battery life of such a device.

Respiratory effort and breathing rate can be also measured in multiple ways. A common method for measuring respiratory effort uses inductance plethysmography, in which a person wears a tightly fitting elastic band around their thorax, whose inductance changes as the person breathes in and out. A limitation of the method from a convenience point of view is that the person has to wear a band, and remains connected to the associated electronic recording device via wires. An alternative system for measuring respiratory effort is to use impedance pneumography, in which the impedance change of the thorax is measured. The limitation of this technology, is that it requires electrodes to be attached to the body, and has an active electrical component which needs to be carried by the subject.

For cardiorespiratory fitness assessment, it is also useful to measure gross bodily motion, as that is an overall indicator of daily activity and exercise intensity. The most common technique for measuring free-living activity is to use accelerometers, which can measure acceleration. When carried by a person, such devices can provide a useful indicator of the overall duration and intensity of the person's movement, such devices are often sold commercially as pedometers (step-counters). A limitation of this technology is the requirement for the person to carry the device, and the limitations of the algorithms for converting measured acceleration into activity patterns.

What is needed then, is a method, system and apparatus for measuring heart rate, respiratory rate and effort, and motion, and which overcomes various limitations of conventional approaches.

SUMMARY

This disclosure provides various embodiments and aspects of an apparatus, system, and method for monitoring heart rate, breathing and motion. In one embodiment, a sensor unit can be either worn (for ambulatory use), or placed in a fixed position (e.g., as part of an exercise cycling machine). The sensor communicates with a processor and display and, in one aspect, the sensor, processor, and display may be physically implemented in the same unit. The processor may be used to extract information about heart rate, breathing and motion, and higher order information (e.g., the current heart rate relative to previous epochs). The display is configured to provide feedback to the user, such as displaying current heart rate or breathing rate. Feedback may also be provided using sound (e.g., a beep for every heart beat detected). In one aspect, a complete system may include one or more of a motion sensor (for detection of general bodily movement, respiration, and heart rate); a processing capability (to derive signals directly related to cardiac activity, breathing and motion, and hence to derive parameters such as breathing rate, heart rate, and movement); a display capability (to provide visual feedback); an auditory capability (to provide acoustic feedback, e.g., a tone whose frequency varies with breathing, or a beep with every detected heart beat); and/or a communications capability (wired or wireless) to transmit acquired data to a separate unit. This separate unit may be configured to carry out the processing, display and auditory functions mentioned above.

In one or more embodiments, the disclosed system for measuring, analyzing, and displaying respiration, cardiac activity, and bodily movement, comprises one or more sensors configured to receive a reflected radio-frequency signal off a living subject, a processor configured to analyze the reflected signal to determine a measurement of physiological activity of the living subject; and a display arranged to provide selected information relating to the physiological activity to a user of the system. The system may further comprise a transmitter that generates the radio frequency signals that are reflected off the living subject, and the power levels emitted by the system are safe for continuous use with humans. The monitored physiological activity corresponds to movements which can include breathing, cardiac activity, and large movements of the body (such as an arm swinging)

In another embodiment, a method for measuring, analyzing, and displaying respiration, cardiac activity, and bodily movement includes receiving radio-frequency signals reflected from a human subject; analyzing the reflected signals to produce measurements relating to respiration, cardiac activity, and bodily movement of the human subject; and providing selected information to a user of the system.

BRIEF DESCRIPTION OF THE DRAWINGS

Embodiments of the disclosure will now be described with reference to the accompanying drawings in which:

FIG. 1(a) shows an embodiment of the system as an upper arm cuff band; FIG. 1(b) shows the system as a clip-on device which can be attached to a shirt-pocket; FIG. 1(c) shows an example of the device worn as a pendant around the neck; FIG. 1(d) illustrates the cardiorespiratory monitor in a treadmill fitness system; FIG. 1(e) gives an example of the cardiorespiratory monitor embedded in an exercise cycle machine; and FIG. 1(f) shows the device as a wristwatch-like device while swimming.

Figure 4:
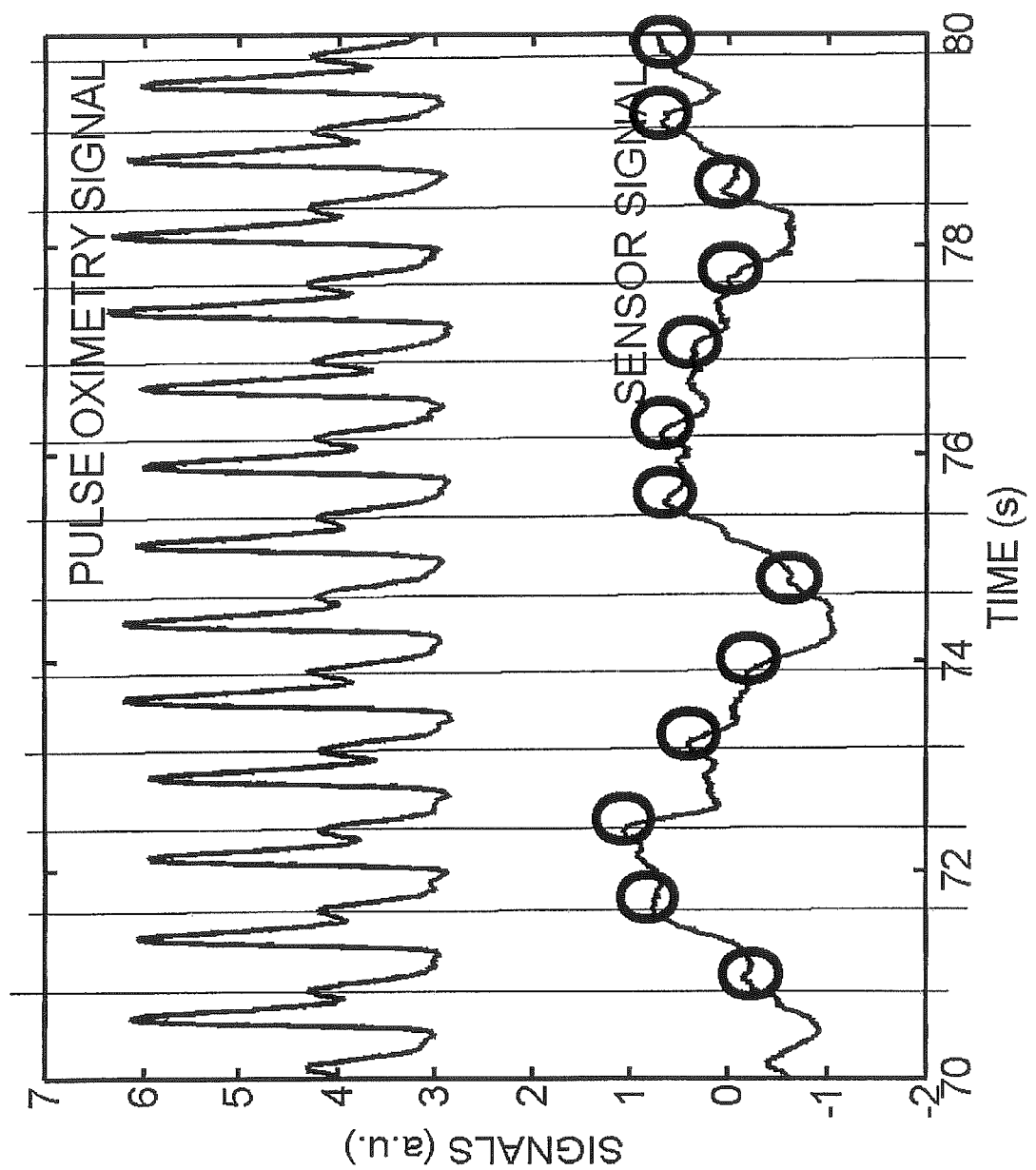

The upper curve of FIG. 4 shows the time course of a photoplethysmographic signal obtained from an adult subject, where each heart beat is associated with a distinctive pattern and the lower curve of FIG. 4 illustrates the signal obtained simultaneously from the same subject at a distance of several meters, showing that there are separate respiration and cardiac signals.

Figure 5:
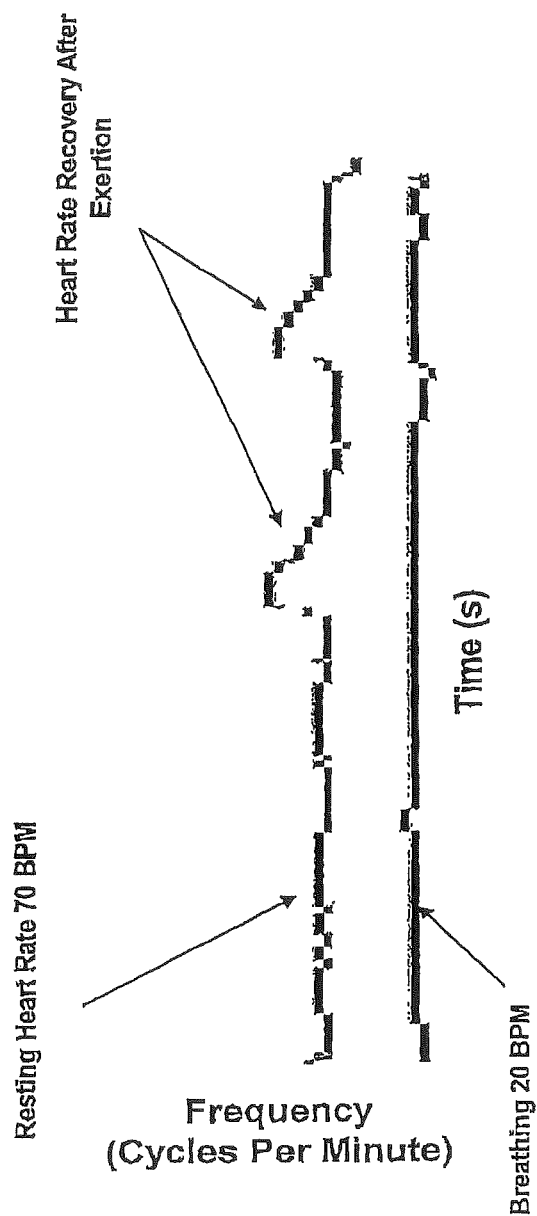

FIG. 5 illustrates the result of applying a technique for accessing and visualizing the breathing and cardiac information using a time-frequency representation such as the short-time Fourier transform and a peak-finding algorithm.

Figure 2:
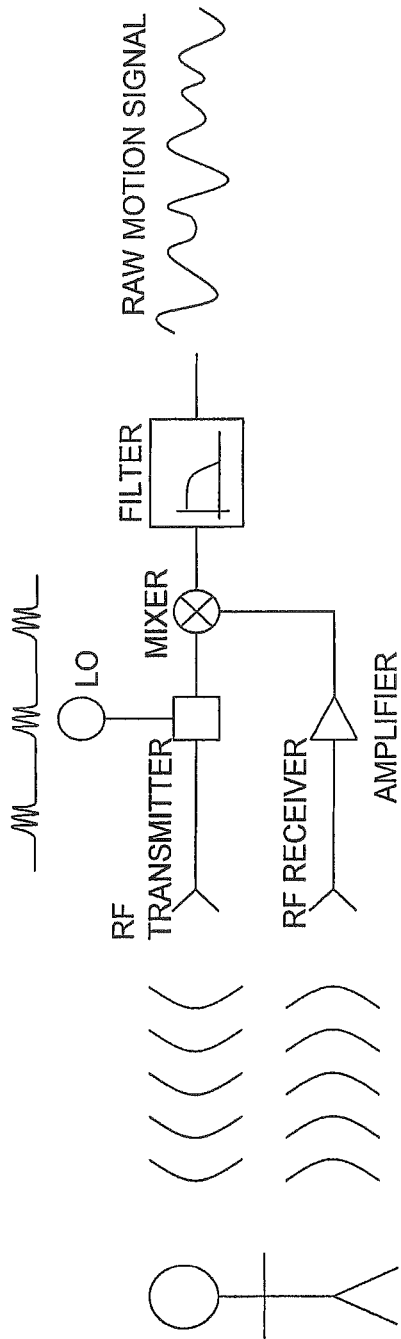
FIG. 2 provides a schematic representation of a sensor element of one embodiment.
Figure 6:
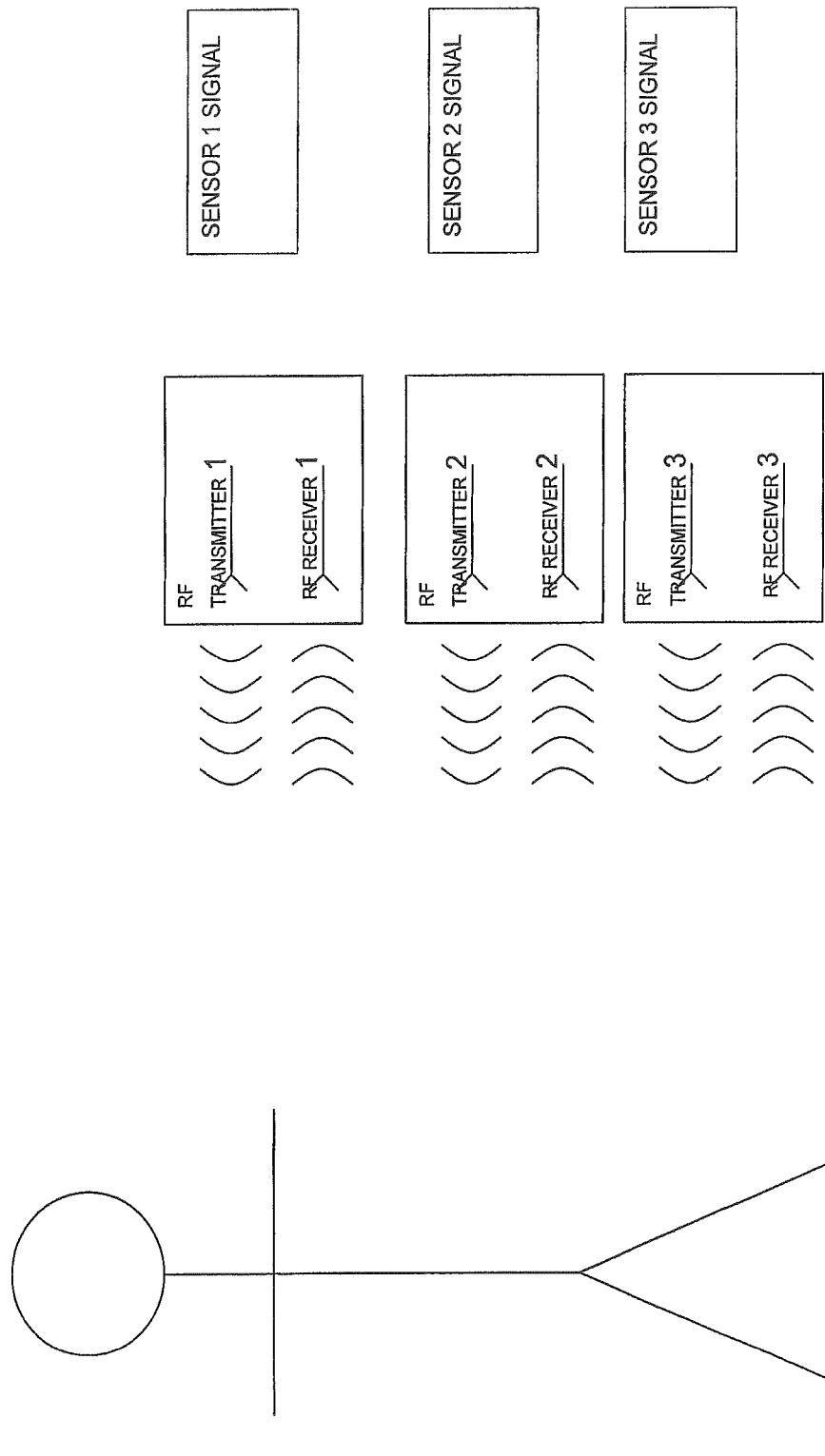

FIG. 6 provides a schematic of the system when multiple radio frequency (RF) blocks similar to those depicted in FIG. 2 are used for transmission and reception of the radio waves.

Figure 7A:
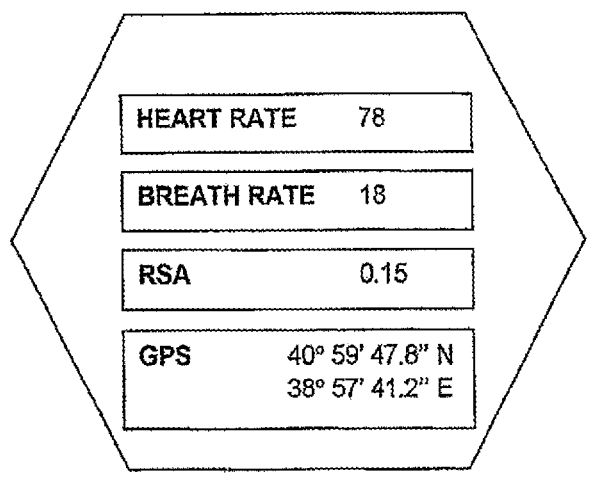

FIG. 7A illustrates a schematic of the display for the system.

Figure 7B:
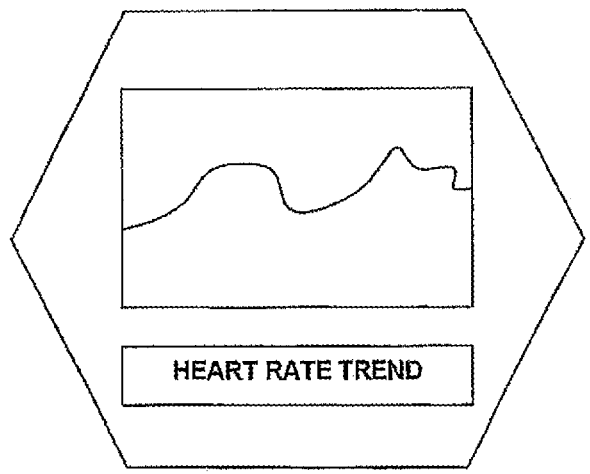

FIG. 7B illustrates a schematic of the display for the system.

Figure 8:
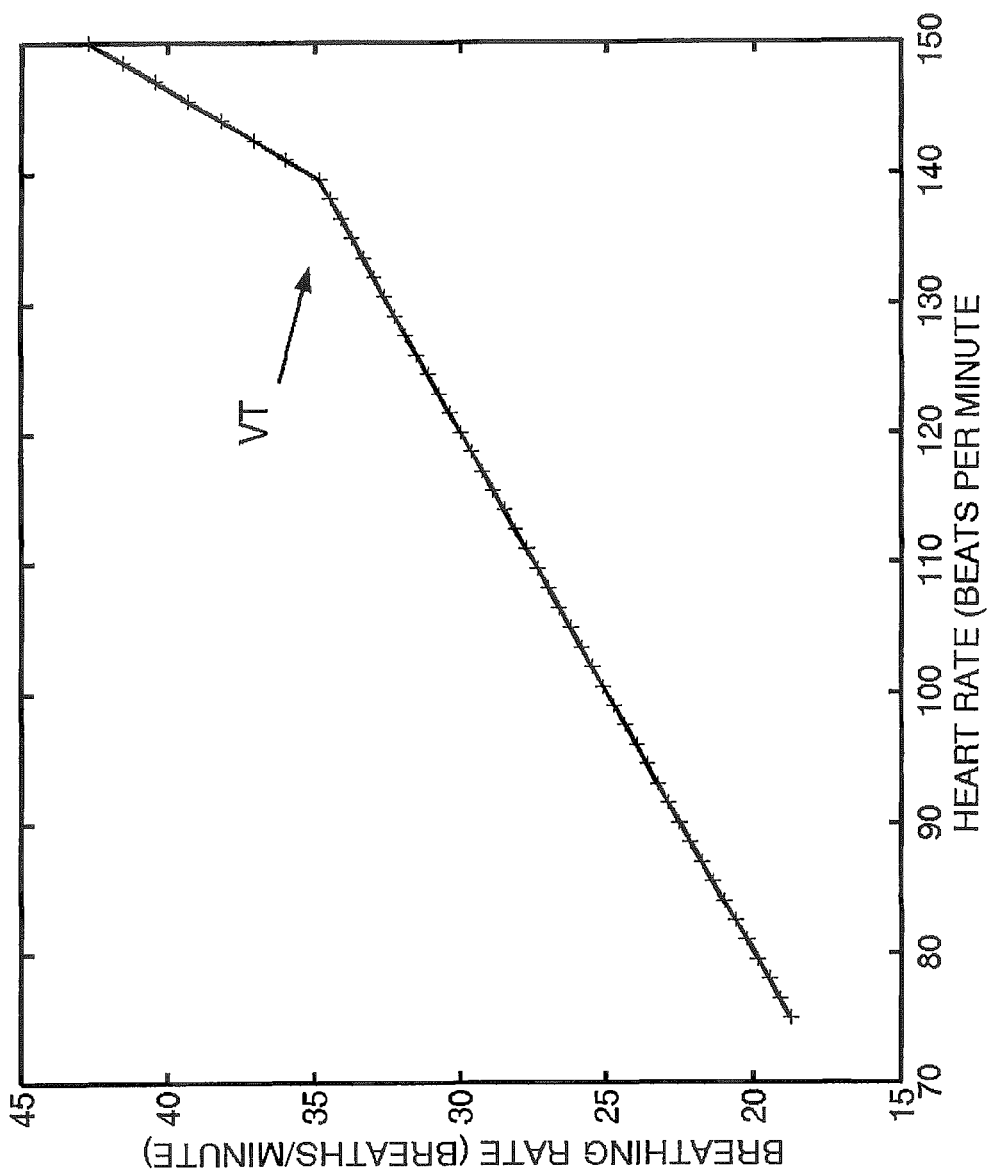

FIG. 8 shows a schematic of how the system can calculate a parameter related to a ventilatory threshold.

DETAILED DESCRIPTION

Figure 1:
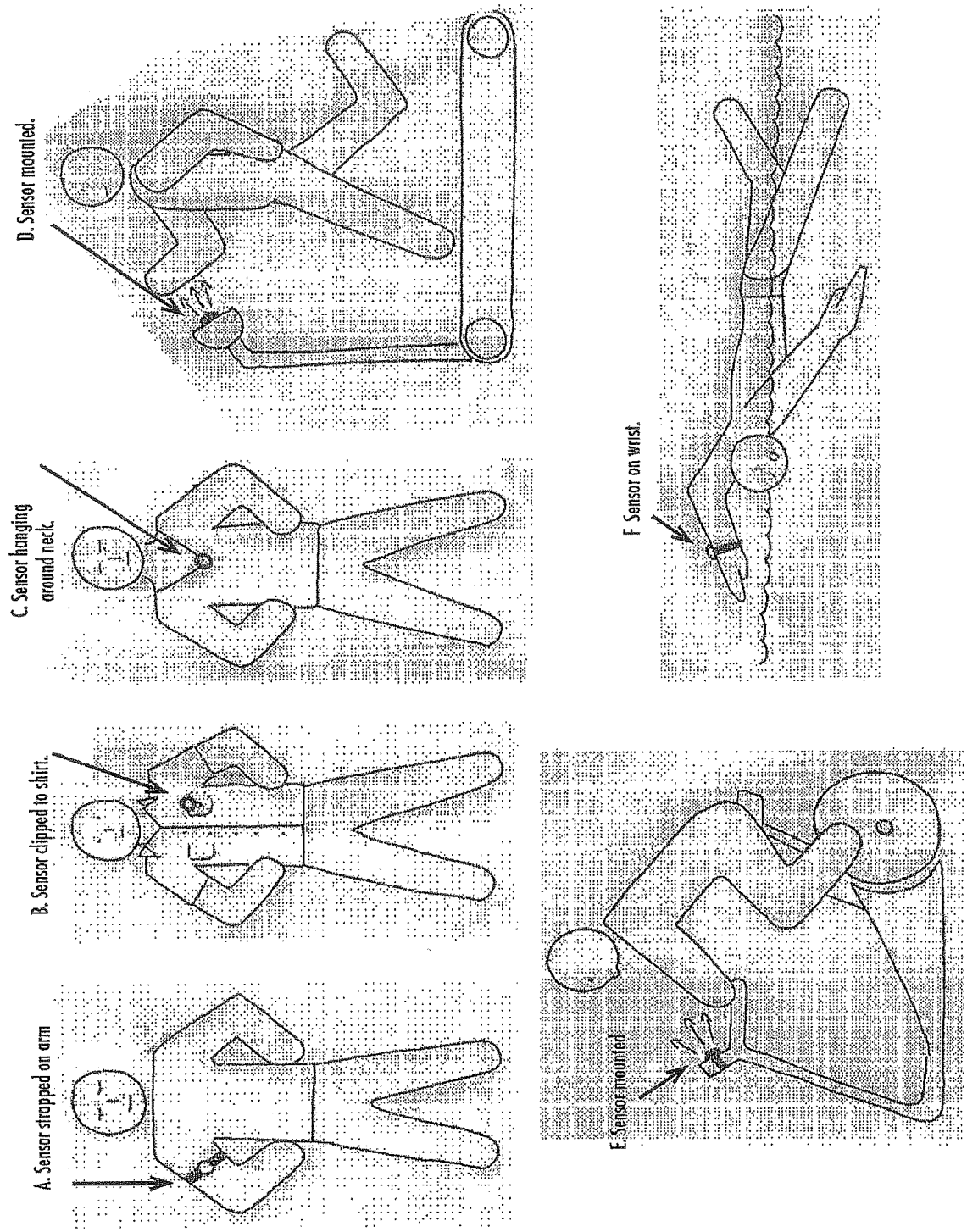
FIG. 1 is a diagram illustrating a schematic of how a system of an embodiment might be used in assessment of exercise and activity.

FIG. 1 is a diagram illustrating a schematic of various environments in which the system might be used in assessment of exercise and activity. First, the device can be used in ambulatory applications (where the person can move freely since they are wearing the cardiorespiratory monitor). FIG. 1(a) shows an embodiment of the system as an upper arm cuff band. FIG. 1(b) shows the system as a clip-on device which can be attached to a shirt-pocket. FIG. 1(c) shows an example of the device worn as a pendant around the neck, FIG. 1(d) illustrates the cardiorespiratory monitor in a treadmill fitness system, FIG. 1(e) gives an example of the cardiorespiratory monitor embedded in an exercise cycle machine and FIG. 1(f) shows the device as a wristwatch-like device while swimming. The device can also be configured for use with other known exercise equipment.

FIG. 2 provides a schematic representation of an exemplary sensor element. The sensor element uses radio-frequency sensing and processing to extract bodily motion associated with breathing and heart rate. The body motion associated with respiration is readily observable as breathing induces motion of the thorax and abdomen. The motion associated with cardiac activity is less obvious, but physiologists use the term "ballistocardiogram" to refer to the pressure wave apparent at the surface of the skin due to the cardiac contraction. This small motion can be detected by a sensitive motion sensor.

The system transmits a radio-frequency signal towards a person. The reflected signal is then received, amplified and mixed with a portion of the original signal, and the output of this mixer is then low pass filtered. The output of this mixer can therefore be considered as a processed time-domain signal derived from the reflected radio-frequency signal. This resulting signal contains information about the movement, respiration and cardiac activity of the person, and is referred to as the raw sensor signal. In FIG. 2, the radio frequency sensor components of the system are illustrated with a pulsed continuous wave signal for illustration. In an alternative embodiment, the system may also use quadrature transmission in which two carrier signals 90 degrees out of phase are used. In the limits that the pulse becomes very short in time, such a system can be recharacterized as an ultrawideband (UWB) radio-frequency sensor. Improved signal-to-noise ratio can also be obtained by using a continuous wave system, in which the RF signal is continuously transmitted.

Figure 3:
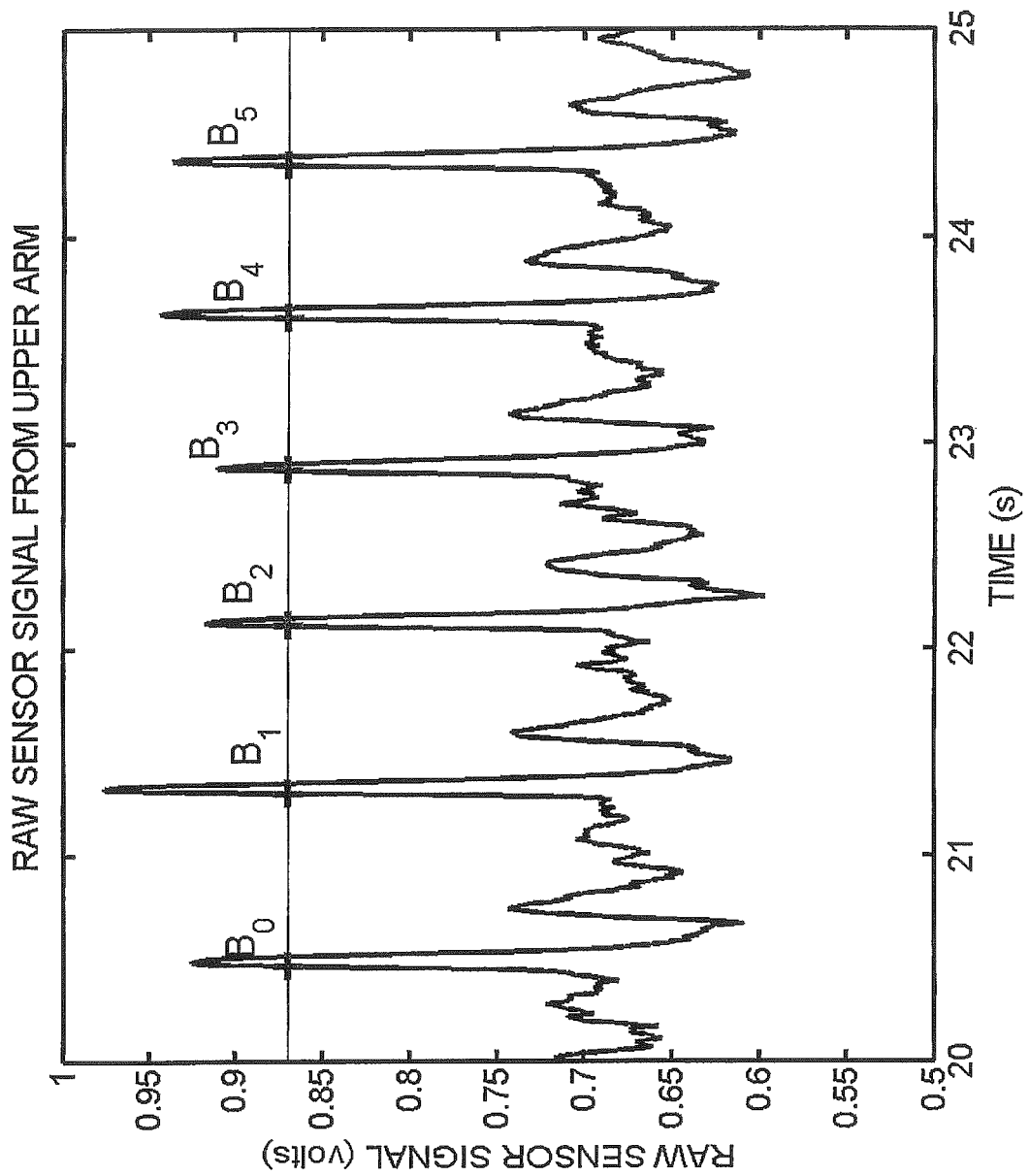
FIG. 3 provides a representative raw sensor signal obtained when the sensor is close to the surface of the body (e.g., within 5 cm).

FIG. 3 gives a representative raw sensor signal obtained when the sensor is close to the surface of the body (e.g., within 5 cm). The dominant components in the received raw sensor signal will be the ballistocardiogram, and the relative motion of the sensor and person. To reduce the relative motion, the sensor unit may be mechanically fixed to the skin using an elastic restraining mechanism, or similar. FIG. 3 is an example of the raw sensor signal with a dominant ballistocardiogram component (in this case, measured at the inside of the elbow on the upper arm). This represents 5 seconds of data collected using a 26 GHz pulsed continuous wave prototype of the system. In such cases, heart beats will be determined by a threshold passing technique (a pulse is associated with the point where the signal is greater or less than the threshold). In more complex (but typical cases), the ballistocardiogram will present a more complicated but repeatable pulse shape. Therefore a pulse shape template, implemented, for example, by a matched filter, can be correlated with the acquired cardiac signal, and places where the correlation is high will be used as the heart beat locations. Accordingly the system recognizes cardiac beats of the living subject by identifying peaks in the processed time-domain signal, or by carrying out a time-domain correlation of the received signal with a prototypical cardiac signal, or by other means. This processing results in a series of time markers identifying the occurrence time of each heart beat. These time markers can be used by a processor to audibly signal each heart beat of the living subject, or to light up an intermittent icon on a display.

Given a time marker of when each event occurred, calculating heart rate is possible. For the signal shown in FIG. 3, we will label the point at which the signal crosses a threshold as a cardiac event time $B_n$ (where n is the beat number). From that we can calculate the instantaneous heart rate as $1/BB_n$ where $BB_n=B_n-B_{n-1}$ (the interbeat interval). In practice, it may be more useful to define the average heart rate over a time epoch (e.g., 10 seconds). This can be achieved by counting the number of beats which occurred within a 10-second window, and then dividing by 10 to obtain the average number of beats per second. For the example shown in FIG. 3, 5.9 beats occurred within a five second window, so that the reported heart rate is $(5.9/5) \times 60=71$ beats per minute.

When the device is further away from the body (e.g., 1 meter or greater) the received raw sensor signal will be a combination of gross bodily movement, respiration, and cardiac activity. The upper curve of FIG. 4 shows the time course of a photoplethysmographic signal obtained from an adult subject, where each heart beat is associated with a distinctive pattern. The lower curve of FIG. 4 illustrates the signal obtained simultaneously from the same subject at a distance of several meters, and shows that there are separate respiration and cardiac signals. Specifically, the circles highlight the skin movement associated with each cardiac beat. The skin motion is typically aligned with the dichrotic peak in the pulse waveform.

In cases of usage further away from the body, as described above the received raw signal contains information about breathing and heart rate, as well as gross bodily motion. A technique for accessing and visualizing the breathing and cardiac information is to use a time-frequency representation such as the short-time Fourier transform and a peak-finding algorithm. The processor can also be configured to recognize the physiological activity of the living subject using frequency domain processing of the received signals. The detailed description of this is provided below, but broadly it consists of taking the spectrum of an epoch centered at time $t_1$, and finding spectral peaks which correspond best to the expected breathing and cardiac frequencies. For that epoch, the two peaks can be noted, and considered as the cardiac and respiratory frequency at time $t_1$. A new epoch can then be formed which overlaps with the previous epoch, but which is now centered at $t_2$, and two new frequencies can be calculated which form the cardiac and respiratory frequency at time $t_2$. FIG. 5 illustrates the result of applying this technique to 50 seconds of data, with a window length of 20 seconds, and an overlap of 19 seconds. The breathing component at about 20 breaths per minute, and the cardiac component at approximately 70 beats per minute can be tracked over time.

FIG. 6 provides a schematic of the system when multiple radio frequency (RF) blocks are used for transmission and reception of the radio waves. In this schematic, there are three independent RF blocks, each capable of receiving and transmitting the radio waves. The individual RF blocks are similar to that shown earlier in FIG. 2. They will generate independent copies of the overall signal from the person being sensed, so that independent motion components can be extracted using signal processing (e.g., breathing, cardiac signal, and upper body motion). Note that the antennas can also transmit at separate frequencies if required. Physical separation of the antennas (e.g., by greater than a quarter wavelength) will also make the transmission paths statistically independent.

FIG. 7 illustrates a schematic of the display for the system. The system will typically display parameters such as current heart rate, current breathing rate, and the degree of respiratory sinus arrhythmia. Since the system may be easily integrated with a device capable of measuring position (e.g., using the Global Positioning System—GPS), position may also be displayed on the system output. The system will also have the capability to display useful trends for the user, such as the heart rate over the past hour, the values of RSA over the last week, etc. A further advantage of incorporating position information is that it allows the system to be used in standard tests of fitness. For example, a good marker of general cardiovascular health is the "one mile fitness test". In this, the person walks a mile briskly, and records their pulse at the end of the one-mile. A positioning system will automatically inform the person when they have walked a mile, and record the heart rate at that time. Similarly, in clinical applications, the six-minute walk test is routinely used. In this, a person is asked to walk for six minutes at their own pace, and the distance covered is a marker of their general cardiovascular health. An integrated positioning system will automatically keep a track of the distance covered, and the heart and respiration rate during that period. So the utility of the system can be augmented by including a positioning system configured to monitor a location of the living subject, and to simultaneously track their physiological activity.

FIG. 8 shows a schematic of how the system can calculate a parameter related to ventilatory threshold. The device can record the heart rate and breathing rate over a period of exercise. At the end of the exercise, the device can plot heart rate versus the average breathing rate seen at that heart rate. A schematic representation of such a curve is shown in FIG. 8. If the exercise intensity is close to the person's maximum, then the curve can be used to identify a "kink" at which breathing rate increases more rapidly with respect to heart rate. The breathing rate at which this occurs can act as a surrogate of ventilatory threshold (VT). The value of the this parameter can be tracked over the course of weeks or months, as the person undergoes a fitness program.

In one embodiment, the system includes a sensor unit, and a monitoring and display unit where results can be analysed, visualized and communicated to the user. The sensor unit and the display/monitoring unit can be incorporated into a single stand-alone device, if required. The device may include one or more of a motion sensor (for detection of general bodily movement, respiration, and heart rate); a processing capability (to derive signals directly related to cardiac activity, breathing and motion, and hence to derive parameters such as breathing rate, heart rate, and movement); a display capability (to provide visual feedback); an auditory capability (to provide acoustic feedback, e.g., a tone whose frequency varies with breathing, or a beep with every detected heart beat); a communications capability (wired or wireless) to transmit acquired data to a separate unit. This separate unit can carry out the processing, display and auditory capability mentioned above.

More specifically, the typical sensor will include one or more radio-frequency Doppler sensors, which transmit radio-frequency energy (typically in the range of 100 MHz to 100 GHz), and which use the reflected received signal to construct a motion signal. For ease of explanation, we will first restrict our discussion to the case where only one sensor unit is used. The principle by which this works is that a radio-frequency wave $$s(t)=u(t)\cos(2\pi f_c t+\theta) \qquad (1)$$

is transmitted from the unit. In this example, the carrier frequency is $f_c$, t is time, and $\theta$ is an arbitrary phase angle. u(t) is a pulse shape. In a continuous wave system, the value is always one, and can be omitted from Eq. (1). More generally, the pulse will be defined as $$u(t) = \begin{cases} 1, t \in [kT \; kT + T_p], k \in Z \\ 0 \end{cases} \qquad (2)$$

where T is the period width, and $T_p$ is the pulse width. Where $T_p \ll T$, this becomes a pulsed continuous wave system. In the extreme case, as $T_p$ becomes very short in time, the spectrum of the emitted signal becomes very wide, and the system is referred to as an ultrawideband (UWB) radar or impulse radar. Alternatively, the carrier frequency of the RF transmitted signal can be varied (chirped) to produce a so-called frequency modulated continuous wave (FMCW) system.

This radio frequency signal is generated in the sensor system using a local oscillator coupled with circuitry for applying the pulse gating. In the FMCW case, a voltage controlled oscillator is used together with a voltage-frequency converter to produce the RF signal for transmission. The coupling of the RF signal to the air is accomplished using an antenna. The antenna can be omnidirectional (transmitting power more-or-less equally in all directions) or directional (transmitting power preferentially in certain directions). It can be advantageous to use a directional antenna in this system so that transmitted and reflected energy is primarily coming from one direction. The system is compatible with various types of antenna such as simple dipole antennas, patch antennas, and helical antennas, and the choice of antenna can be influenced by factors such as the required directionality, size, shape, or cost. It should be noted that the system can be operated in a manner which has been shown to be safe for human use. The system has been demonstrated with a total system emitted average power of <1 mW (0 dBm) and lower. The recommended safety level for RF exposure is 1 mW/cm$^2$. At a distance of 1 meter from a system transmitting at 0 dBm, the equivalent power density will be at least 100 times less than this recommended limit.

In all cases, the emitted signal will be reflected off objects that reflect radio waves (such as the air-body interface), and some of the reflected signal will be received back at the transmitter. The received signal and the transmitted signal can be multiplied together in a standard electronic device called a mixer (either in an analog or digital fashion). For example, in the CW case, the mixed signal will equal $$m(t)=\gamma \cos(2\pi f_c t)\cos(2\pi f_c t+\phi(t)) \quad (3)$$

where $\phi(t)$ is the path difference of the transmitted and received signals (in the case where the reflection is dominated by a single reflective object), and $\gamma$ is the attenuation experienced by the reflected signal. If the reflecting object is fixed, then $\phi(t)$ is fixed, and so is m(t). In the case of interest to us, the reflecting object (e.g., chest) is moving, and m(t) will be time-varying. As a simple example, if the chest is undergoing a sinusoidal motion due to respiration:

$$resp(t)=\cos(2\pi f_m t) \quad (4)$$

then the mixed signal will contain a component at $f_m$ (as well as a component centred at $2f_c$ which can be simply removed by filtering). The signal at the output of the low pass filter after mixing is referred to as the raw sensor signal, and contains information about motion, breathing and cardiac activity.

The amplitude of the raw sensor signal is affected by the mean path distance of the reflected signal, leading to detection nulls and peaks in the sensor (areas where the sensor is less or more sensitive). This effect can be minimised by using quadrature techniques in which the transmitter simultaneously transmits a signal 90 degrees out of phase (the two signals will be referred to as the I and Q components). This will lead to two reflected signals, which can be mixed, leading eventually to two raw sensor signals. The information from these two signals can be combined by taking their modulus (or other techniques) to provide a single output raw sensor signal.

In the UWB case, an alternative method of acquiring a raw sensor signal may be preferred. In the UWB case, the path distance to the most significant air-body interface can be determined by measuring the delay between the transmitted pulse and peak reflected signal. For example, if the pulse width is 1 ns, and the distance from the sensor to the body is 0.05 m, then the total time $m(\tau)$ elapsed before a peak reflection of the pulse will be $0.1/(3\times10^8)$ s=0.33 ns. By transmitting large numbers of pulses (e.g., a 1 ns pulse every 1 µs) and assuming that the path distance is changing slowly, we can derive a raw sensor signal as the average of the time delays over that period of time.

In this way, the radio-frequency sensor can acquire the motion of the part of the body at which the system is aimed. Directional selectivity can be achieved using directional antennas, or multiple RF transmitters. The combined motion of the thorax (which is a combination primarily of a respiration and cardiac signal) acquired in this way using a pulsed continuous wave system is shown in the lower curve of FIG. 4. We stress however that a continuous wave, an FMCW, or a UWB radar can also obtain similar signals.

Moreover, since the bulk of the reflected energy is received from the surface layer of the skin, this motion sensor can also obtain the ballistocardiogram, which is the manifestation of the beating of the heart at the surface of the skin due to changes in blood pressure with each beat. An example of a surface ballistocardiogram obtained with an RF motion sensor has already been shown in FIG. 3. In that case, the ballistocardiogram is emphasized by the sensor being close to the skin (upper arm) and no respiratory component is visible.

In order to improve the qualities of the measured sensor signals, the physical volume from which reflected energy is collected by the sensor can be restricted using various methods. For example, the transmission antenna can be made "directional" (that is, it transmits more energy in certain directions), as can the receiver antenna. A technique called "time-domain gating" can be used to only measure reflected signals which arise from signals at a certain physical distance form the sensor. A practical way to implement this is to ensure that received signal is mixed with a transmitted signal over a predefined period of time. For example, imagine that a 12 ns pulse is emitted at time t=0 ns. If the reflecting object is 150 cm away, the reflected pulse will be first received after 10 ns (since it takes light 10 ns to cover 300 cm). Assume a second object 300 cm away whose detection is not desired. The reflected pulse from this second object will not first arrive till time t=20 ns. Therefore if mixing between the transmitted and received pulses is only allowed in the time period from t=10 ns to t=15 ns, all the information received will relate only to the first reflecting object. Frequency domain gating can be used to restrict motions of the reflected object above a certain frequency.

In a simple embodiment of the system, a single antenna will be used, with a single carrier frequency. This antenna will act as both the transmit and receive antenna. However, in principle, multiple receive and transmit antennas can be used, as can multiple carrier frequencies. In the case of measurements at multiple frequencies (e.g., at 500 MHz and 5 GHz) the lower frequency can be used to determine large motions accurately without phase ambiguity, which can then be subtracted from the higher-frequency sensor signals (which are more suited to measuring small motion, such as the cardiac signature).

All of these sensor inputs are fed into the unit for processing and display purposes, and for possible transmission to a separate unit (the monitoring unit).

The system then uses its processing capability to combine the sensor inputs to provide a number of useful outputs, and to display these outputs in a meaningful manner. These steps are carried out in the following manner.

The cardiorespiratory monitor is primarily designed to provide information about heart rate and respiration. When the person is moving, the sensor signal will often be dominated by motion, in which case processing is required to reduce motion artefact problems. A preferred technique for calculating respiration and heart beat activity in the presence of noise is as follows.

A raw signal is acquired for an epoch of desired length (e.g., 20 seconds). The spectrum of this period of the signal is estimated using a technique such as the smoothed averaged periodogram. In general, since respiration occurs typically at a frequency from 10 to 25 breaths per minute (about 0.15-0.45 Hz), and cardiac activity occurs in the range 60-120 beats per minute (1 to 2 Hz), the spectrum of the signal will have two peaks in the ranges 0.15-0.4 Hz, and 1 to 2 Hz. The frequency at which these peaks occur can be referred to as the breathing frequency and the heart rate respectively, for that epoch. The results of the spectral analysis for each epoch can be arranged in time to form a time-frequency respiration plot, which is a useful means of visualizing the overall respiratory and cardiac activity. Note that the epochs can overlap, so that a breathing frequency and cardiac frequency can be calculated at arbitrary times (e.g., FIG. 5 shows the case where the analyzed epochs are one second apart).

The presence of large motion artefacts may confound the processing described above, so in some cases it may be necessary to preprocess the signal to reduce the effect of motion artefact. Since large movements lead to large-magnitude signals in the processed time domain, a processor can be configured to measure the energy content of a filtered signal, so that periods of bodily motion of the living subject are recognized by comparing the energy content to a predetermined energy value. A method for doing this is to prefilter the epoch with a linear high pass filter (to remove all frequencies below 0.05 Hz, for example). An alternative would be to median filter the data with a window length of 10 seconds, and remove the median filtered signal from the original signal. Alternatively, we can recognise periods of motion by their high energy content. These periods of motion may lead to artifacts in the processed signal, so suitable pectral analysis that removes periods of measurement can be used. Specifically, when calculating the spectrum of the epoch, the data from these high motion sections is not included in the estimation (using a technique called Lomb's periodogram which provides spectral estimates from data with missing segments).

An alternative processing technique for improving the accuracy of the heart beat and respiration detection is to acquire multiple signals from multiple sensors. This is particularly beneficial in the case of high motion artefact, such as the case when the system is used in a treadmill setting with person jogging in the field of the sensors. In such a case, a preferred solution is to have multiple sensors (e.g, m, where m might typically be in the range four to sixteen, but can vary from one to any number). In practice (for cost reasons), it is probably efficient to have a single transmit antenna, and multiple receive antennas only, rather than having each antenna be both transmitting and receiving. Likewise it may be beneficial to have the antenna or antennas generate RF signals at multiple frequencies. However, an embodiment of the method is where one transmitter is used, and m signals are received in the sensor (each path will experience a different phase delay and amplitude change). A further useful embodiment of the system is one in which there are multiple sensors operating at different frequencies, wherein a relatively low frequency is used to estimate a large bodily movement of the living subject, and a relatively high frequency is used to estimate a smaller movement of the living subject. For example, a sensor operating at 1 GHz would be useful for detecting movement in the centimeter range, while a sensor operating in the same system at 100 GHz could help detect movement of millimetres.

A useful model is to collect the m received signal into a vector of signals x:

$$x = \begin{bmatrix} x_1 \\ x_2 \\ \vdots \\ x_m \end{bmatrix}$$

It can be reasonable assumed that each signal represents a mixture of reflections from multiple sources (e.g., one from breathing, one from cardiac activity, one from left arm movement, etc.). Therefore, the received signals represent a linear mixture of sources w, so that $$w = Ax \text{ where } A = \begin{bmatrix} a_{11} & a_{12} & \cdots & \\ a_{21} & & & \\ & & \ddots & \\ & \cdots & & a_{mm} \end{bmatrix}$$

In practice, we are interested in obtaining the signals w, since they will cleanly separate the different components of interest. A critical factor which aids us in this analysis is that the source signals are independent (i.e., the cardiac signal is independent of breathing, which is independent of atm motion, for example). There are many algorithms which map the received x back to w, under this assumption, and these are referred to as Independent Component Analysis (ICA) techniques. In particular, we can further optimise our solution by imposing certain constraints on the source signals (e.g., it should have a dominant frequency in the range 0.15 to 0.25 Hz). Such algorithms are called constrained ICA algorithms. A useful survey of techniques in ICA analysis can be found in "independent component analysis for biomedical signals," C. J. James and C. W. Hesse, Physiological Measurement vol. 26 (1), R15-R39, February 2005.

As well as determining respiration rate and amplitude, cardiac rate, and motion, the system provides for means to combine signals for calculation of further useful outputs. For example, a useful marker of overall cardiorespiratory health is respiratory sinus arrhythmia (RSA). This measures the influence of breathing on heart rate, and the stronger the coupling, the better the overall cardiorespiratory health. In general, there is utility in configuring a processor to calculate a parameter of respiratory sinus arrhythmia using the measured heart rate and breathing rate information. One approach may be to calculate a parameter of respiratory sinus arrhythmia using cross-spectral analysis of measured heart rate and breathing rate signals.

However, a variety of techniques exists for calculating RSA. One embodiment for this system is as follows.

An epoch of measurement (e.g., 60 seconds) is taken, over which the person's activity is fairly constant. The coherence between the cardiac signal and the respiratory signal is obtained (coherence is typically defined as the ratio of the cross spectral density of two signals divided by the square root of the power spectral densities of the signals taken separately.) The highest value of the coherence in a defined band (e.g., 0.15-0.25 Hz) is taken as a measure of the coupling between heart rate and respiration. This coherence value can be tracked across different exercise sessions, or compared against a population mean.

A further useful measure of cardiorespiratory performance obtained by the system is the estimation of ventilatory threshold from heart rate measurements only, or combinations of heart rate and breathing rate. The system can be configured to calculate useful parameters of cardiorespiratory performance (such as ventilatory threshold) by relating a measured heart rate to a measured breathing rate over a defined period of measurement. A preferred embodiment for capturing ventilatory threshold from combined heart rate and breathing rate is to examine a curve of cardiac beats per breathing cycle versus breathing rate. In such a curve, there is a characteristic kink, which occurs at the frequency corresponding to the ventilatory threshold.

Finally, the system provides means for communicating useful information to its user. The display means may be in a format such as a wristwatch, with parameters such as current heart rate, current breathing rate, and position. The user may also have the ability to view trend screens, which show charts of previous heart rates over different time scales, previous breathing rates, as well as derived parameters such as estimated RSA coherence. In some use cases, it is beneficial to design an enclosure which can contain one or more sensors, the processor, and the display. This enclosure could be suitable for being held in a hand of the user for convenience of use. The enclosure could also incorporate other functionality such as telecommunications or positioning systems (e.g., a cellular phone handset would be a specific embodiment of such an enclosure).

STATEMENT OF INDUSTRIAL APPLICABILITY

This disclosure has application in the medical, safety, and sports fitness fields, for example, by monitoring motion, breathing, and heart rate of living beings, e.g., humans, in a convenient and low-cost fashion. Such monitoring is useful, for example, in the assessment of cardiorespiratory markers of fitness and activity of humans.

What is claimed is:

1. A system for monitoring physiological parameters of a living subject, the system comprising:
one or more sensors configured to receive a radio frequency signal reflected off the living subject;
one or more processors configured to determine a measurement of respiration or cardiac activity of the living subject, in part, by:
measuring an energy content of a raw sensor signal derived from a transmitted radio-frequency signal and the reflected radio frequency signal;
identifying a period of bodily motion by comparing the measured energy content to a predetermined energy value;
calculating a short-time Fourier transform of an epoch of the raw sensor signal, wherein the epoch comprises the identified period of bodily motion, and wherein a segment of the raw sensor signal that corresponds to the identified period of bodily motion is excluded from the calculation of the short-time Fourier transform; and
finding a spectral peak within the short-time Fourier transform that corresponds to an expected breathing frequency or an expected cardiac frequency; and
a display configured to provide information relating to the determined measurement of respiration or cardiac activity to a user.

2. The system of claim 1, wherein the one or more sensors are further configured to transmit the transmitted radio frequency signal towards the living subject.

3. The system of claim 2, further comprising:
a mixer configured to mix the reflected radio frequency signal and the transmitted radio frequency signal to produce a mixed signal,
wherein the raw sensor signal is derived from the mixed signal.

4. The system of claim 3, further comprising:
a low-pass filter configured to filter the mixed signal to obtain the raw sensor signal.

5. The system of claim 3, further comprising at least one additional sensor configured to receive a second signal reflected from the living subject.

6. The system of claim 5, wherein the mixer is configured to multiply the transmitted radio-frequency signal, the reflected radio-frequency signal, and the second reflected signal to produce the mixed signal.

7. An apparatus for determining physiological parameters of an activity of a living subject, the apparatus comprising:
at least one sensor configured to receive a reflected radio frequency signal off the living subject;
a device configured to calculate a location associated with the living subject and track a measure of a distance travelled by the living subject;
one or more processors configured to determine a measurement of respiration or cardiac activity of the living subject, in part, by:
measuring an energy content of a raw sensor signal derived from a transmitted radio-frequency signal and the reflected radio frequency signal;
identifying a period of bodily motion by comparing the measured energy content to a predetermined energy value;
calculating a spectrum of an epoch of the raw sensor signal, wherein the epoch comprises the identified period of bodily motion, and wherein a segment of the raw sensor signal that corresponds to the identified period of bodily motion is excluded from the calculation of the spectrum; and
finding a spectral peak within the spectrum that corresponds to an expected breathing frequency or an expected cardiac frequency; and
a display to provide information associated with the determined measurement of respiration or cardiac activity to a user over the measure of distance travelled by the living subject.

8. A system for providing information to a user regarding respiratory and cardiac parameters of a living subject, the system comprising:
one or more sensors configured to receive one or more reflected radio frequency signals off the living subject;
one or more processors configured to determine one or more measurements of respiration or cardiac activity of the living subject, in part, by:
measuring an energy content of a raw sensor signal derived from one or more transmitted radio-frequency signals and the one or more reflected radio frequency signals;
identifying a period of bodily motion by comparing the measured energy content to a predetermined energy value;
estimating a spectrum of an epoch raw sensor signal, wherein the epoch comprises the identified period of bodily motion, and wherein a segment of the raw sensor signal that corresponds to the identified period of bodily motion is excluded from the estimation of the spectrum; and
identifying a peak in the estimated spectrum that corresponds to an expected breathing frequency or an expected cardiac frequency; and
feedback means for providing selected information about the determined one or more measurements of respiration or cardiac activity.

9. The system of claim 8, wherein the feedback means comprises a display configured to provide visual information relating to the determined one or more measurements of respiration or cardiac activity.

10. The system of claim 9, wherein the display is configured to visually signal a heart rate or a breathing rate of the living subject.

11. The system of claim 8, wherein the one or more sensors are further configured to transmit the one or more transmitted radio-frequency signals towards the living subject.

12. The system of claim 8, wherein the one or more sensors comprise multiple sensors operating at different transmission frequencies.

13. The system of claim 12, wherein a plurality of signals provided by the multiple sensors are processed simultaneously to produce the raw sensor signal.

14. The system of claim 8, wherein the feedback means is configured to audibly signal a heartbeat of the living subject.

15. The system of claim 8, wherein the raw sensor signal is derived from a mixed signal produced by multiplying the one or more transmitted and reflected radio frequency signals.

16. The system of claim 8, further comprising:
an enclosure configured to enclose the one or more sensors, the one or more processors, and the feedback means.

17. The system of claim 16, wherein the enclosure is suitable for being held in a hand of the user.

18. A method for providing information to a user regarding respiratory or cardiac parameters of a living subject, the method comprising:
receiving, with at least one sensor, one or more radio frequency signals reflected from the living subject;
measuring, with at least one processor, an energy content of a raw sensor signal derived from one or more transmitted radio-frequency signal and the one or more reflected radio-frequency signals;
identifying, with the at least on processor, a period of bodily motion by comparing the measured energy content to a predetermined energy value;
estimating, with the at least one processor, a spectrum of an epoch of the raw sensor signal, wherein the epoch comprises the identified period of bodily motion, and wherein a segment of the raw sensor signal that corresponds to the identified period of bodily motion is excluded from the estimation of the spectrum;
determining, with at least one processor, one or more measurements of respiration or cardiac activity of the living subject by identifying a peak in the estimated spectrum that corresponds to an expected breathing frequency or an expected cardiac frequency; and
providing, with a feedback means, selected information about the determined one or more measurements of respiration or cardiac activity.

19. The system of claim 1, wherein the expected breathing frequency ranges from 0.15 Hz to 0.45 Hz, and wherein the expected cardiac frequency ranges from 1 Hz to 2 Hz.

20. The system of claim 1 further comprising:
a high-pass filter configured to prefilter the raw sensor signal to remove one or more portions of the raw sensor signal that correspond to periods of bodily motion.

21. The system of claim 20, wherein the high-pass filter removes frequencies below 0.05 Hz.

22. The system of claim 1, wherein the one or more processors are configured to apply a median filter to the raw sensor signal and calculate the short-time Fourier transform from the median filtered raw sensor signal.

23. The system of claim 1, wherein the one or more processors are further configured to calculate respiratory sinus arrhythmia or ventilatory threshold based on the determined measurement of respiration or cardiac activity.

24. The system of claim 23, wherein the one or more processors are configured to determine measurements of respiration and cardiac activity, and wherein the one or more processors are configured to calculate respiratory sinus arrhythmia or ventilatory threshold based on the measurements of respiration and cardiac activity.

25. The system of claim 24, wherein the one or more processors are configured to calculate respiratory sinus arrhythmia, in part, by obtaining a coherence between the measurements of respiration and cardiac activity.

26. The system, of claim 24, wherein the one or more processors are configured to calculate ventilatory threshold, in part, by identifying a kink in a curve relating the measurements of respiration and cardiac activity over a defined period of time.

27. The system of claim 1, wherein the one or more processors are configured to determine a plurality of measurements of respiration or cardiac activity of the living subject over a period of time, in part, by:
calculating a plurality of short-time Fourier transforms of a plurality of overlapping epochs of the raw sensor signal, wherein at least one of the plurality of overlapping epochs comprises the identified period of bodily motion, and wherein the segment of the raw sensor signal that corresponds to the identified period of bodily motion is excluded from the calculations of the plurality of short-time Fourier transforms; and
finding spectral peaks within each of the plurality of short-time Fourier transforms that correspond to the expected breathing frequency or the expected cardiac frequency.

28. The system of claim 27, wherein the display is further configured to provide trend information to the user that relates to the determined plurality of measurements of respiration or cardiac activity of the living subject over the period of time.

29. The system of claim 28, wherein the display is configured to provide the trend information to the user as a chart.

30. The system of claim 29, wherein the chart illustrates a breathing rate of the living subject over the period of time.

31. The system of claim 29, wherein the chart illustrates a heart rate of the living subject over the period of time.

32. The system of claim 1 further comprising:
a device configured to track a measure of a distance travelled by the living subject,
wherein the display is further configured to provide information associated with the determined measurement of respiration or cardiac activity to the user over the measure of distance travelled by the living subject.

33. The apparatus of claim 11, wherein the apparatus is configured to be worn on a portion of the living subject's anatomy.

34. The system of claim 8 further comprising:
a high-pass filter configured to prefilter the raw sensor signal to remove one or more portions of the raw sensor signal that correspond to periods of bodily motion.

35. The system of claim 8, wherein the one or more processors are configured to apply a median filter to the raw sensor signal and calculate the spectrum from the median filtered raw sensor signal.

36. The system of claim 8, wherein the feedback means provides one or more charts of previously determined measurements of respiration or cardiac activity along with the determined one or more measurements of respiration or cardiac activity.

37. The system of claim 8, wherein the one or more processors are configured to determine a plurality of measurements of respiration or cardiac activity of the living subject over a period of time, in part, by:
estimating a plurality of spectrums of a plurality of overlapping epochs of the raw sensor signal, wherein at least one of the plurality of overlapping epochs comprises the identified period of bodily motion, and wherein the segment of the raw sensor signal that corresponds to the identified period of bodily motion is excluded from the estimation of the plurality of spectrums, and identifying peaks within each of the plurality of estimated spectrums that correspond to the expected breathing frequency or the expected cardiac frequency.

38. The system of claim 37, wherein the feedback means provides trend information to the user that relates to the determined plurality of measurements of respiration or cardiac activity of the living subject over the period of time.

39. The system of claim 38, wherein the feedback means provides the trend information to the user as a chart.

40. The system of claim 8 further comprising:
a device configured to track a measure of a distance travelled by the living subject,
wherein the feedback means provides information associated with the determined measurement of respiration or cardiac activity to the user over the measure of distance travelled by the living subject.

41. The method of claim 18 further comprising:
prefiltering, with a high-pass filter, the raw sensor signal to remove one or more portions of the raw sensor signal that correspond to periods of bodily motion.

42. The method of claim 18, wherein a median filter is applied to the raw sensor signal and the spectrum is calculated from the median filtered raw sensor signal.

43. The method of claim 18 further comprising:
providing, with the feedback means, one or more charts of previously determined measurements of respiration or cardiac activity along with the determined one or more measurements of respiration or cardiac activity.

44. The method of claim 18 further comprising:
estimating, with the at least one processor, one or more additional spectrums of one or more additional overlapping epochs of the raw sensor signal, wherein the segment of the raw sensor signal that corresponds to the identified period of bodily motion is excluded from the estimation of the one or more additional spectrums; and
determining, with at least one processor, one or more additional measurements of respiration or cardiac activity of the living subject by identifying peaks within each of the one or more additional estimated spectrums that correspond to the expected breathing frequency or the expected cardiac frequency.

45. The method of claim 44 further comprising:
providing, with the feedback means, trend information to the user that relates to the determined measurements of respiration or cardiac activity of the living subject over a period of time.

46. The method of claim 45, wherein the trend information is provided to the user as a chart.

47. The method of claim 18 further comprising:
tracking a geographic distance travelled by the living subject; and
providing, with the feedback means, information associated with the determined one or more measurements of respiration or cardiac activity to the user over the measure of distance travelled by the living subject.

* * * * *